United States Patent [19]

Capecchi et al.

[11] Patent Number: 5,292,514

[45] Date of Patent: Mar. 8, 1994

[54] AZLACTONE-FUNCTIONAL SUBSTRATES, CORNEAL PROSTHESES, AND MANUFACTURE AND USE THEREOF

[75] Inventors: John T. Capecchi, Oakdale; Steven M. Heilmann, Afton; Larry R. Krepski, White Bear Lake; Oh-Seung Kwon, Woodbury; David B. Olson, May Township, County of Washington, all of Minn.

[73] Assignee: Minnesota Mining and Manufacturing Company, St. Paul, Minn.

[21] Appl. No.: 903,367

[22] Filed: Jun. 24, 1992

[51] Int. Cl.$^5$ ............................ A61F 2/14; C08K 5/15
[52] U.S. Cl. .................................... 424/422; 424/423; 424/426; 424/427; 424/428; 424/429; 525/54.2; 525/375; 623/4; 623/5
[58] Field of Search ............... 424/426, 422, 427, 428, 424/429, 423; 525/54.2, 375

[56] References Cited

U.S. PATENT DOCUMENTS

| | | | |
|---|---|---|---|
| 2,714,721 | 8/1955 | Stone, Jr. | 623/51 |
| 4,118,531 | 10/1978 | Hauser | 428/224 |
| 4,304,705 | 12/1981 | Heilmann et al. | 260/30.4 |
| 4,451,619 | 5/1984 | Heilmann et al. | 525/379 |
| 4,485,236 | 11/1984 | Rasmussen et al. | 544/69 |
| 4,528,325 | 7/1985 | Ofstead | 525/60 |
| 4,612,012 | 9/1986 | White | 623/5 |
| 4,613,665 | 9/1986 | Larm | 536/20 |
| 4,618,649 | 10/1986 | Ofstead | 525/60 |
| 4,655,770 | 4/1987 | Gupta et al. | 623/1 |
| 4,673,539 | 6/1987 | Hammar et al. | 264/1.1 |
| 4,715,858 | 12/1987 | Lindstrom | 523/5 |
| 4,772,283 | 9/1988 | White | 632/5 |
| 4,828,563 | 5/1989 | Müller-Lierheim | 623/16 |
| 4,852,969 | 8/1989 | Babirad et al. | 350/96.34 |
| 4,855,234 | 8/1989 | Hendrickson et al. | 435/181 |
| 4,910,277 | 3/1990 | Bambury et al. | 526/260 |
| 4,914,223 | 4/1990 | Rasmussen et al. | 560/49 |
| 4,963,494 | 10/1990 | Hibino et al. | 435/288 |
| 4,979,959 | 12/1990 | Guire | 623/66 |
| 5,032,131 | 7/1991 | Aysta et al. | 623/66 |
| 5,059,654 | 10/1991 | Hou et al. | 525/54.1 |
| 5,064,578 | 11/1991 | Insley et al. | 264/12 |
| 5,081,197 | 1/1992 | Heilmann et al. | 540/471 |
| 5,108,428 | 4/1992 | Capecchi et al. | 623/5 |
| 5,149,806 | 9/1992 | Moren et al. | 544/72 |

FOREIGN PATENT DOCUMENTS

| | | | |
|---|---|---|---|
| 0137686 | 4/1985 | European Pat. Off. | |
| 0392735A2 | 10/1990 | European Pat. Off. | |
| 0392783A2 | 10/1990 | European Pat. Off. | |
| 0407580A1 | 1/1991 | European Pat. Off. | |
| WO87/01040 | 8/1985 | PCT Int'l Appl. | |
| WO89/00032 | 7/1987 | PCT Int'l Appl. | |
| WO90/00887 | 7/1988 | PCT Int'l Appl. | |
| WO90/05018 | 5/1990 | PCT Int'l Appl. | B01D 63/02 |
| WO92/07899 | 10/1990 | PCT Int'l Appl. | |
| 2215614A | 2/1988 | United Kingdom | |

OTHER PUBLICATIONS

Wente, "Superfine Thermoplastic Fibers", *Industrial Engineering Chemistry*, vol. 48, pp. 1342–1346, (1956).
Wente et al., "Manufacture of Superfine Organic Fibers", Naval Research Laboratory Report #4364, 1954.

(List continued on next page.)

*Primary Examiner*—Thurman K. Page
*Assistant Examiner*—Peter F. Kulkosky
*Attorney, Agent, or Firm*—Gary L. Griswold; Walter N. Kirn; John H. Hornickel

[57] ABSTRACT

Azlactone-functional substrates, (especially hydrogels), mammalian body implants, and methods of making and using them are disclosed. The azlactone-functional substrates are the reaction product of substrates having azlactone-reactive nucleophilic surfaces and a multifunctional azlactone composition having at least two azlactone moieties, where at least one moiety covalently couples to the azlactone-reactive nucleophilic surface and at least one moiety remains available for further nucleophilic reaction, such as with a biologically active material. A preferred use of azlactone-functional hydrogel is as the optical element of a corneal prosthesis which enhances epithethial cell growth.

32 Claims, 1 Drawing Sheet

OTHER PUBLICATIONS

Tabata et al., "Immobilization of Callagen onto Polymer Surfaces Having Hydroxyl Groups", *Biomaterials*, vol. 7, pp. 234–238, May 1986.

Rasmussen et al., "Polyazlactones" Encyclopedia of Polymer Science and Engineering, vol. 11, John Wiley, pp. 558–571 (1988).

Trinkaus-Randall et al., "Development of a Biopolymeric Keratoprosthetic Material", *Inv. Ophth. and Vis. Sci.*, 1988, vol. 29, pp. 394–400.

Kobayashi et al., "Covalent Immobilization of Proteins on to the Surface of Poly(Vinyl Alcohol) Hydrogel" *Biomaterials*, vol. 12, Oct. 1991.

Kobayashi et al., "Immobilization of Proteins onto PVA Surface" Translated from Abstract Presented at Meeting in May 1988 of Polymer Science Society of Japan.

Scouten, "Affinity Chromatography-Bioselective Adsorption on Inert Matrices" *Chemical Analysis* vol. 59, (John Wiley & Sons, N.Y.), pp. 48–49, 68–69, and 74–75 (1981).

STN International Abstract of Japanese Kokai JP 02070711 (1990) concerns benzophenone compounds.

AZLACTONE-FUNCTIONAL SUBSTRATES, CORNEAL PROSTHESES, AND MANUFACTURE AND USE THEREOF

FIELD OF THE INVENTION

This invention relates to substrates, especially hydrogels, having azlactone-functional surfaces, mammalian body implants, (e.g., corneal prostheses), comprising such azlactone-functional hydrogels, and methods of making and using them.

BACKGROUND OF THE INVENTION

Mammalian body implants, such as corneal prostheses, (also known as keratoprostheses), are very useful to replace degenerated or injured mammalian tissue if the remainder of the mammalian body accepts the presence of such implant and if the biocompatible implant performs the function of the replaced tissue in an acceptable manner.

Corneal prostheses are especially vital for the continued functioning of a mammal, especially a human being, because a degenerated or injured cornea obscures vision.

While there have been attempts to provide synthetic corneal prostheses, currently none are deemed acceptable by governmental regulatory agencies due to their inability to provide an acceptable replacement for natural cornea transplants obtained from cadavers. Often these devices have failed because of erosion and necrosis of the adjacent tissue, chronic inflammation and epithelialization of the anterior chamber.

Optimally, the anterior surface of a keratoprosthesis should support the adherence and proliferation of corneal epithelial cells, resulting in an intact epithelial layer which is continuous with the surrounding host epithelium. A continuous layer of epithelium permits maintenance of the normal precorneal tear film, ensures a good optical surface and provides a barrier against microbial invasion.

A prior effort has been to provide a corneal prosthesis using poly(vinyl alcohol) hydrogel as an optical element and a porous outer skirt secured to the periphery of the element. European Patent Publication 0 333 344 (Capecchi et al.), the European counterpart to U.S. Pat. No. 5,108,428 discloses this corneal prosthesis and identifies the desire to coat or laminate the anterior surface with a basement membrane component(s) to facilitate growth of epithelial cells on it. Coating is preferably performed by adsorption or chemical attachment or integration during polymerization with basement membrane component(s) prior to seeding of corneal epithelial cells on the anterior surface. Acceptable basement membrane components include laminin, fibronectin, Type I collagen, Type IV collagen, or a cell-free extract prepared from extracellular matrix of corneal epithelial cells.

SUMMARY OF THE INVENTION

The need exists to optimize interaction of cells with mammalian body implants. The present invention solves the problem of providing a biocompatible mammalian body implant, especially a corneal prosthesis, which is capable of providing surfaces for optimum mammalian cell growth, especially epithelial cell growth.

One aspect of the present invention is a novel azlactone-functional substrate which is functional for reaction with nucleophilic compounds.

Another aspect of the present invention is a novel azlactone-functional hydrogel which is useful as a component in a mammalian body implant.

Another aspect of the present invention is a multifunctional azlactone composition useful for the preparation of an azlactone-functional substrate, especially an azlactone-functional hydrogel.

Another aspect of the present invention is a mammalian body implant, especially a corneal prosthesis, which is prepared using an azlactone-functional hydrogel and a porous outer skirt of a nonwoven polyolefin web secured at the periphery of the hydrogel on its posterior surface.

Another aspect of the present invention is a method of preparing an azlactone-functional substrate, especially an azlactone-functional hydrogel.

Another aspect of the present invention is a method of preparing a mammalian body implant using an azlactone-functional hydrogel and the porous outer skirt of nonwoven polyolefin web.

Another aspect of the present invention is a composition useful as an ultraviolet absorbing monomer employed with an azlactone-functional hydrogel.

"Substrate" means a composition having nucleophilic surfaces and capable of reaction with an azlactone-functional composition.

"Hydrogel" means a substrate which is a hydrophilic composition, regardless of its state of hydration, which is capable of swelling, but not dissolving, in water.

"Multi-functional azlactone composition" means a composition having at least two azlactone moieties available for nucleophilic reaction.

"Azlactone" means an oxazolinone moiety of Formula I:

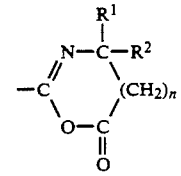

wherein
$R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon atoms and 0 to 3 S, N, and nonperoxidic O heteroatoms, or $R^1$ and $R^2$ taken together with the carbon to which they are joined can form a carbocyclic ring containing 4 to 12 ring atoms, and
n is an integer 0 or 1.

"Azlactone-functional" means that a reaction between a multi-functional azlactone composition and a substrate results in a covalent bond between nucleophilic surfaces of the substrate and at least one azlactone moiety of the multifunctional azlactone composition, such that at least one azlactone moiety remains available for further nucleophilic reaction with a biologically active material.

"Biologically active material" means a chemical composition having azlactone-reactive, nucleophilic-functional groups and capable of reacting in a manner which affects biological processes, especially mammalian cells. Nonlimiting examples of biologically active materials are substances which are biologically, immunochemically, physiologically, or pharmaceutically active. Examples of biologically active materials include proteins, peptides, polypeptides, antibodies, antigenic substances, enzymes, cofactors, inhibitors, lectins, hormones, receptors, coagulation factors, amino acids, histones, vitamins, drugs, cell surface markers, and substances which interact with them.

"Activated substrate" means an azlactone-functional substrate of Formula II:

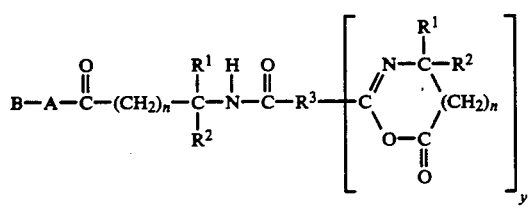

wherein $R^1$, $R^2$, and n are as previously defined,
wherein y is at least one and is the number of azlactone moieties less at least one,
wherein $R^3$ is a bridging group capable of covalently connecting a plurality of azlactone moieties, and
wherein B is the substrate and A is the residue of the azlactone-reactive nucleophilic group on the substrate, such as O, S, or $NR^4$, wherein $R^4$ is hydrogen or an alkyl group containing from 1 to 4 carbon atoms.

"Bridging group" means a group comprising (a) an alkylene group having up to 14 carbon atoms; (b) an arylene group having up to 10 carbon atoms; (c) a cycloalkylene group having up to 6 carbon atoms; (d) a group resulting from the Michael reaction of a Michael donor nucleophilic compound with a plurality of 2-alkenyl azlactone Michael acceptors, where the Michael donor nucleophilic compound has at least two azlactone-reactive moieties; or (e) a combination of the above-listed bridging groups. Nonlimiting examples of alkylene, arylene, and cycloalkylene groups are disclosed in "Polyazlactones" by J. K. Rasmussen, S. M. Heilmann, L. R. Krepski in *Encyclonedia of Polymer Science and Engineering*, Vol. 11, 2nd Ed., 1988, John Wiley & Sons, Inc., pp. 558-571, the disclosure of which is incorporated by reference. Nonlimiting examples of such Michael donor nucleophilic compounds include thiols and secondary amines as disclosed in U.S. Pat. No. 4,485,236 (Rasmussen et al.) incorporated by reference herein, or combinations thereof; or carbon acids, enamines, imides, and nitrogen heterocycles (as disclosed in copending, coassigned U.S. patent application Ser. No. 07/500,768 (Moren et al.) incorporated by reference herein), now U.S. Pat. No. 5,149,806 (Moren et al.), or combinations thereof.

A feature of the present invention is that azlactone-functional substrates are capable of reacting with nucleophilic biologically active materials, such as extracellular matrix proteins, such as laminin, fibronectin, Type I collagen, Type IV collagen, or a cell-free extract prepared from extracellular matrix of corneal epithelial cells, in order to prepare a mammalian body implant for implantation and successful cell growth.

Another feature of the present invention is that the azlactone-functional substrate couples biologically active materials in a manner which permits further biochemical interaction with living cells.

Another feature of the present invention is that coupling of biologically active materials to a hydrogel modifies surfaces of the hydrogel in a manner which permits biocompatible mammalian body implantation. The hydrogel can be any desired shape for mammalian body implantation. The surface modification enhances cell growth upon implantation, thus allowing articles of the present invention to be useful as a mammalian body implant.

An advantage of the present invention is that the use of azlactone-functional hydrogels as elements of a corneal implant is superior to prior methods of enhancing cell growth.

Thus, the invention provides a mammalian body implant comprising a hydrogel having azlactone-reactive nucleophilic surfaces, a multi-functional azlactone composition covalently coupled to the azlactone-reactive nucleophilic surfaces, and a biologically active material coupled to the multi-functional azlactone composition.

The invention also provides an azlactone-functional substrate comprising a substrate having azlactone-reactive nucleophilic surfaces and a multi-functional azlactone composition covalently coupled thereto in a manner such that at least one azlactone moiety remains available for further nucleophilic reaction.

The invention also provides a biologically active substrate comprising the reaction product of an activated substrate described above and a biologically active material.

The invention also provides a multi-functional azlactone composition selected from the group consisting of tris[[2-[N-2-(4,4-dimethyl-2-oxazoline-5-one-2-yl)ethyl, N-isopropyl]-2-amino]ethyl]amine and N,N',N''-tris-2-(4,4-dimethyl-2-oxazoline-5-one-2-yl)ethyl-bis-(N,N''-isopropyl-2-aminoethyl)amine.

The invention also provides a benzophenone ultraviolet light absorber selected from the group consisting of 2-allyloxy-4,4'-dimethoxy-2-hydroxy benzophenone and 3-allyl-2,2'-dihydroxy-4,4'-dimethoxy benzophenone.

The invention also provides a method of making an azlactone-functional hydrogel comprising the steps of (a) forming a hydrogel in a dehydrated state comprising a composition having azlactone-reactive nucleophilic surfaces and reacting a multi-functional azlactone composition with the azlactone-reactive nucleophilic surfaces of the hydrogel in a dehydrated state in a manner that retains at least one azlactone moiety remaining available for further nucleophilic reaction.

The invention also provides a method of forming a mammalian body implant comprising the steps of forming an azlactone-functional hydrogel according to the method described above and reacting a biologically active material with at least one azlactone moiety.

Further description of embodiments of the invention follows with reference to the Drawings.

EMBODIMENTS OF THE INVENTION

Substrates

Figure 1:
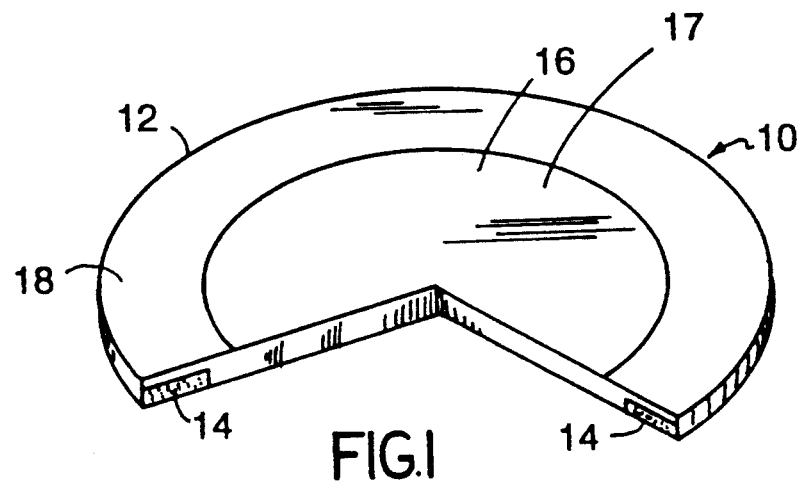
FIG. 1 is a diagrammatic perspective view, partially broken away, of a corneal prosthesis according to the invention.

Substrates useful for the present invention can be any natural or synthetic composition which has azlactone-reactive, nucleophilic surfaces due to the presence of azlactone-reactive, nucleophilic moieties such as hydroxyl, amine, or thiol moieties. Nonlimiting examples of substrates include naturally occurring compositions, such as cellulose (and modified cellulose derivatives), agarose, dextran, chitin and chitosan; synthetic compositions such as polymers derived from monomers such as hydroxyethyl methacrylate, hydroxypropyl acrylate, N-methylolacrylamide, allyl alcohol, allyl amine, and N-[3-(N'-isopropyl)aminopropyl] methacrylamide; and polymers derived by modification of polymers such as silica gel and glass particles reacted with γ-triethoxysilylpropylamine, γ-triethoxysilylpropane-1-thiol, or γ-glycidoxypropyltrimethoxysilane (followed by hydroylsis of the epoxide), and hydrogels as defined herein.

Hydrogel

Depending on the type of mammalian body implant, the selection of a useful hydrogel can vary according to desired physical and chemical characteristics. A hydrogel needs azlactone-reactive nucleophilic reaction sites for covalent coupling with an azlactone moiety. Preferably, the azlactone-reactive nucleophilic reaction sites are hydroxyl groups.

Many suitable hydrogel compositions that are biocompatible with mammalian tissues are described in the art. Hydrogels that have been approved by governmental regulatory agencies for use with or in mammalian tissues are preferred. Nonlimiting examples of biocompatible hydrogels that have azlactone-reactive nucleophilic reaction sites for chemical interaction with a multi-functional azlactone composition include poly(-vinyl alcohol) copolymer systems, and poly(vinylpyrrolidone) blends where the other polymer(s) of the blend contain azlactone-reactive nucleophilic surfaces. Ofstead European Published Patent Application No. 0137686A ("Ofstead '686A"), discloses desirable copolymer systems and blends and is incorporated by reference.

Of these possible biocompatible hydrogels, poly(vinyl alcohol) homopolymers and copolymers are preferred, either as bulk material or as coatings on the outer surfaces thereof. Preferred poly(vinyl alcohol) copolymers are described in U.S. Pat. No. 4,618,649 ("Ofstead '649") and U.S. Pat. No. 4,528,325 ("Ofstead '325").

For use as an optical element of a corneal prosthesis, the presently most preferred material is poly(vinyl alcohol-co-vinyl acetate) prepared from a copolymer of vinyltrifluoroacetate (VTFA) and vinyl acetate (VAc) and made according to the methods described in Ofstead '649 (Example 8). The weight ratio of VTFA to VAc can range from about 95:5 to about 99.9:0.1, and preferably between about 97:3 and 99:1. The presently preferred weight ratio is 98.5:1.5, which corresponds to a molar ratio of VTFA:VAC of 97.6:2.4. After solvolysis of VTFA to vinyl alcohol, this poly(vinyl alcohol-co-vinyl acetate) material is a semi-crystalline hydrogel which has azlactone-reactive nucleophilic surfaces of hydroxyl moieties, has an equilibrium water content of 73% in normal saline, tensile strength of 110 kg/cm², initial modulus of elasticity of 10–15 kg/cm², and elongation of 436%. Tensile strength, elongation and modulus were all measured as described at col. 6, line 57 to col. 7, line 4 of Ofstead '649.

Other biocompatible hydrogel materials can be used as optical elements of a corneal prosthesis so long as the water content is greater than 50% (preferably between 65% and 80%) and the tensile strength is greater than 20 kg/cm² (preferably greater than 40 kg/cm²). Further strength-related criteria that preferably are met are a modulus of elasticity between 3 and 115 kg/cm² (preferably 5–15 kg/cm²), and elongation between 100–1000% (preferably greater than 150%).

Other biocompatible hydrogel materials for use as an optical element include other poly(vinyl alcohol) copolymers, e.g., containing maleic anhydride (0–3%) (mole percent) as the comonomer, other hydrogel materials described in Ofstead '649 (see discussion at col. 3, lines 19–50 in particular), other hydrogel materials described in Ofstead '325, other hydrogel materials described in Ofstead '686A (including other blends with poly(vinylpyrrolidone) if the other polymers of the blends have azlactone-reactive nucleophilic moieties), and Hammar et al. U.S. Pat. No. 4,673,539, all of which are hereby incorporated by reference. In the hydrogel materials, the water content and strength properties can be altered by varying the comonomer type and content in the polymer systems or the material ratios in the blends, permitting tailoring to meet physical and chemical characteristics needed for a mammalian body implant generally and a corneal prosthesis particularly.

The presently most preferred poly(vinyl alcohol-co-vinyl acetate) material for use in a corneal prosthesis described above is made by molding of solvent cast discs of the precursor polymer as described in Ofstead '649, although lathe processing of thermally-molded buttons or bulk UV polymerized buttons can also be used. For example, the technique disclosed in Example 14 of U.S. Pat. No. 4,673,539 (Hammar et al.) can be employed for thermally-molded buttons. The VTFA/VAC precursor polymer is then converted to a poly(vinyl alcohol-co-vinyl acetate) hydrogel by a solvolysis reaction.

Preferably, for use as an optical element in a corneal prosthesis, the hydrogel is optically transparent, has a water content between about 50% and about 90%, has a tensile strength of greater than about 20 kg/cm², and has an anterior surface capable of supporting a layer of epithelial cells.

Optionally, other materials can be added to the hydrogel to alter performance characteristics. For example, an ultraviolet light absorbing monomer, such as 2-allyloxy-4,4'-dimethoxy-2'-hydroxy benzophenone (2-allyloxy-BP), 3-allyl-2,2'-dihydroxy-4,4'-dimethoxy benzophenone (3-allyl-BP), 2,2'-dihydroxy-4-methoxy-4'-(2-methacryloyloxyethoxy) benzophenone (MEBP) disclosed in Japanese Kokai 02070711 published Mar. 9, 1990, or 4-(2'-acryloyloxyethoxy)-2-hydroxy benzophenone (commercially available as "Cyasorb UV-2098" from American Cyanamid), can be copolymerized in weight percents ranging from about 0.1 to about 1 part by weight with vinyltrifluoroacetate to form a copolymer which in turn can be blended with preferred precursor polymers in weight ratios of from about 50:50 (precursor:uv-absorbing polymer) to 90:10 to form a uv-absorbing PVA blended hydrogel. Alternatively, the uv-absorbing monomer can be copolymerized with vinyltrifluoroacetate (VTFA) and maleic anhydride (MA) at a 98.5:1.5:0.25 (VTFA:MA:uv-absorbing monomer) weight ratio using thermal initiators such as Lupersol 225 (Pennwalt Corp.) sequentially heating at 40° C. for 12 hours and then at 60° C. for 3 hours. Of the uv-absorbing monomers, 2-allyloxy-BP or 3-allyl-BP are presently preferred because they have the advantage of permanent, non-leachable ultraviolet protection and light absorbance which cuts off sharply at 380 nm.

Multi-Functional Azlactone Composition

Any multi-functional azlactone composition can be useful in the present invention to provide a plurality of azlactones, defined in Formula I above, for reaction with the substrate to produce an azlactone-functional substrate, such as an activated substrate defined in Formula II above, and preferably an azlactone-functional hydrogel. Because the substrate has azlactone-reactive nucleophilic reaction sites, preferably hydroxyl groups, available for covalent reaction with an azlactone moiety, the formation of the bond to covalently couple the multi-functional azlactone composition to the hydrogel uses at least one of the azlactone moieties and leaves at least one other azlactone moiety available for nucleophilic reaction with a biologically active material.

Nonlimiting examples of multi-functional azlactone compositions include homopolymers, copolymers, and oligomers having at least two azlactones as defined in Formula I above. A multi-functional azlactone composition comprises at least two azlactones covalently connected to a bridging group, as defined above.

Nonlimiting examples of suitable multi-functional azlactone compositions and their methods of preparation by Michael Addition are disclosed in U.S. Pat. No. 4,485,236 (Rasmussen et al.), and in copending, coassigned U.S. patent application Ser. No. 07/500,768, now U.S. Pat. No. 5,149,806 (Moren et al.), the disclosures of which are incorporated by reference herein.

Preferably, multi-functional azlactone compositions are homopolymers, copolymers, and oligomers prepared from the Michael Addition of 2-alkenyl azlactone monomers with nucleophilic group-substituted compounds having the formula $(HX)_nR^5$ where $R^5$ is an organic group that has a valence of n and is the residue of a nucleophilic group-substituted compound, $(HX)_nR^5$, in which X is defined above and n is defined below, the residue having a molecular weight up to 20,000, preferably selected from mono-and polyvalent hydrocarbyl (i.e., aliphatic and aryl compounds having 2 to 20 carbon atoms and optionally one to four catenary heteroatoms of oxygen, nitrogen or sulfur, e.g., piperazine, furan, and thiophene), polyoxyalkylene, polyester, polyolefin, polyacrylate, and polysiloxane residues that can optionally all be further substituted by at least one non-nucleophilic group such as cyano, halo, ester, ether, keto, nitro, silyl, sulfide (the carbon-containing groups having up to 10 carbon atoms), and nucleophilic groups including secondary amino groups, hydroxyl groups or mercapto groups; and n is an integer having a value of two to six.

Nonlimiting examples of 2-alkenyl azlactone monomers that can be polymerized to form multi-functional azlactone compositions and their synthesis are disclosed in U.S. Pat. Nos. 4,304,705; 5,081,197; and 5,091,489 (all Heilmann et al.), the disclosures of which are incorporated herein by reference. Suitable 2-alkenyl azlactones include:

2-ethenyl-1,3-oxazolin-5-one,
2-ethenyl-4-methyl-1,3-oxazolin-5-one,
2-isopropenyl-1,3-oxazolin-5-one,
2-isopropenyl-4-methyl-1,3-oxazolin-5-one,
2-ethenyl-4,4-dimethyl-1,3-oxazolin-5-one,
2-isopropenyl-4,4-dimethyl-1,3-oxazolin-5-one,
2-ethenyl-4-methyl-4-ethyl-1,3-oxazolin-5-one,
2-isopropenyl-4-methyl-4-butyl-1,3-oxazolin-5-one,
2-ethenyl-4,4-dibutyl-1,3-oxazolin-5-one,
2-isopropenyl-4-methyl-4-dodecyl-1,3-oxazolin-5-one,
2-isopropenyl-4,4-diphenyl-1,3-oxazolin-5-one,
2-isopropenyl-4,4-pentamethylene-1,3-oxazolin-5-one,
2-isopropenyl-4,4-tetramethylene-1,3-oxazolin-5-one,
2-ethenyl-4,4-diethyl-1,3-oxazolin-5-one,
2-ethenyl-4-methyl-4-nonyl-1,3-oxazolin-5-one,
2-isopropenyl-4-methyl-4-phenyl-1,3-oxazolin-5-one,
2-isopropenyl-4-methyl-4-benzyl-1,3-oxazolin-5-one, and
2-ethenyl-4,4-pentamethylene-1,3-oxazolin-5-one, The preferred 2-alkenyl azlactones include 2-ethenyl-4,4-dimethyl-1,3-oxazolin-5-one (referred to herein as VDM) and 2-isopropenyl-4,4-dimethyl-1,3-oxazolin-5-one (referred to herein as IDM).

Preferably, multi-functional azlactone compositions are prepared using VDM. Nonlimiting examples of VDM-based polymers and oligomers include vinyldimethylazlactone homopolymers and copolymers ("Poly-VDM"), vinyldimethylazlactone oligomers ("Oligo-VDM") prepared by the acid catalyzed polymerization of VDM according to U.S. Pat. No. 5,081,197 incorporated herein by reference, the tris-Michael adduct of VDM and tris-(N'-isopropylaminoethyl)amine having the following formula III and named in this application as tris[[2-[N-2-(4,4-dimethyl-2-oxazoline-5-one-2-yl)ethyl, N-isopropyl]-2-amino]ethyl]amine ("Tris-VDM-T"):

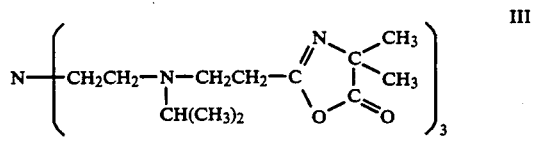

and the tris-Michael adduct of VDM and bis-(N'-isopropylaminoethyl)amine having the following formula IV and named in this application as N,N',N''-tris-2-(4,4-dimethyl-2-oxazoline-5-one-2-yl)ethyl-bis-(N,N''-isopropyl-2-aminoethyl)amine ("Tris-VDM-B"):

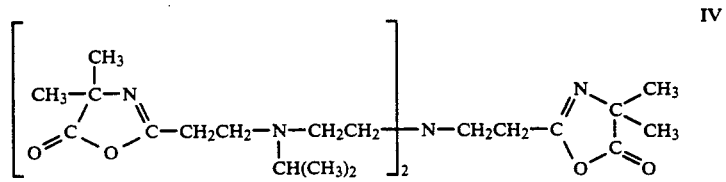

Of these preferred multi-functional azlactone compositions prepared using VDM, Tris-VDM-T is presently preferred.

Reaction of a multi-functional azlactone composition with a hydrogel preferably occurs with the hydrogel in a substantially dehydrated state and can occur at temperatures ranging from about 25° C. to about 300° C. for times ranging from about 1 min. to about 24 hours at ambient, elevated, or reduced pressures and under ambient or inert atmospheric conditions. Preferably, the temperatures range from about 50° C. to about 200° C. Preferably, the reaction times range from about 30 min. to about 3 hours. Preferably, the reaction vessel pressures are ambient. Preferably, the reaction atmosphere is inert to azlactone functionality, using $N_2$ or another gas in anhydrous condition.

Corneal Prostheses

A corneal prosthesis of the present invention includes an optical element having at least an anterior surface which is azlactone-functional and a porous outer skirt secured to the periphery of the element on the posterior surface thereof.

Referring to FIG. 1, there is shown a corneal prosthesis 10 including optical element 12 and porous outer skirt 14. Optical element 12 includes a full depth optically-transparent central portion 16 and a thinner outer portion 18 that overlies skirt 14 which extends around the periphery of prosthesis 10. The anterior surface 17 of optical element 12 is azlactone-functional.

The optical element 12 has an optically transparent central portion 16 and an anterior surface 17 that is capable of supporting a layer of epithelial cells The outer skirt 14 is used to secure the optical element 12 to the patient's surrounding tissue and is sufficiently porous to permit cell ingrowth and tissue attachment.

In preferred embodiments, the optical element 12 is made of a poly(vinyl alcohol) copolymer hydrogel described above with an anterior surface 17 having a multi-functional azlactone composition described above covalently coupled thereto.

In another aspect, the prosthesis 10 also includes a layer of epithelial cells covering the anterior surface 17 of the optical element 12. Preferably, such cells are attached to the anterior surface 17 via coupling of such cells to a biologically active material, such as a basement membrane component, after the biologically active material has been coupled to the azlactone-functional anterior surface 17 of optical element 12. The use of a basement membrane component, (most likely protein) facilitates the growth of epithelial cells on it.

STRUCTURE, MANUFACTURE, AND USE OF CORNEAL PROSTHESES

Optical Element

Optical element 12 is made of an optically transparent hydrogel material described above having a water content between 50% and 90%, a tensile strength of greater than 20 kg/cm$^2$ and an anterior surface capable of supporting a layer of epithelial cells. U.S. Pat. No 5,108,428 (Capecchi et al.), incorporated by reference herein, describes the desired properties of the optical element and the advantages of providing a layer of epithethial cells thereon. The use of an azlactone-functional anterior surface of the present invention to couple a biologically active material for enhancement of cell growth unexpectedly improves the ability of the anterior surface 17 to support a layer of epithelial cells thereon.

The material of optical element 12 preferably is a hydrogel made from the hydrogel materials described above.

Porous Skirt

Porous outer skirt 14 is preferably made of a coherent mass of melt blown fibers having an interconnected network of pores substantially as described in U.S. Pat. No. 5,108,428 (Capecchi et al.) ("Capecchi '428"). The presently most preferred materials for porous skirt 14 are polybutylene (e.g., available under the trade designation Shell 8010) or a polybutylene/polypropylene blend (80%/20%). Preferably, the polymeric material used to form the melt blown fibers also contain an antioxidant, such as Irganox 1010 branded antioxidant, commercially available from Ciba Geigy Corporation of Hawthorn, N.Y. The antioxidant is dry blended at about 1 percent by weight into the mixture of resins prior to feeding the resin mix into the extruder.

The skirt 14 is preferably made according the description contained in capecchi '428 with reference to FIG. 4A thereof and Example 11 therein. Also, U.S. Pat. No. 4,118,531 (Hauser), van Wente, "Superfine Thermoplastic Fibers", Industrial Engineering Chemistry, Vol. 48, pages 1342 et seq. (1956), and Report No. 4364 of the Naval Research Laboratories, published May 25, 1954 entitled "Manufacture of Superfine organic Fibers" by van Wente et al., the disclosures of which are hereby incorporated by reference, and Example 5 below describe methods of making melt blown microfiber web.

Manufacture of Corneal Prostheses

Capecchi '428 generally describes the manufacture of the corneal prosthesis, except that in accordance with the present invention, the anterior surface 17 of the optical element 12 is azlactone-functional and has been reacted with a biologically active material suitable for enhancing epithethial cell growth. Preferably, the optical element 12 (prior to the solvolysis step, described in Ofstead '649, which step causes water-swelling) is formed to shape in the presence of a ring of blown fiber web skirt 14. After preparing a film of the precursor polymer, at a thickness less than the specified central portion 16 thickness desired to accommodate swelling during solvolysis and hydration, using a spin casting drum, blown fiber web is cut to fit and placed in the drum next to the film. While the drum is rotated, a small amount of a solvent which is a solvent for the polymer of the optical element 12 and a nonsolvent for the skirt 14 (e.g., acetone) is injected to wet the blown fiber web and dissolve the surface of the film allowing the blown fibers to become embedded in the film. The solvent must be evaporated quickly to prevent total saturation of the blown fiber web and the complete dissolution of the film, which would occlude pores of the skirt 14. Then spinning continues in the spin casting drum, uncovered, for about 30 to about 60 minutes. After solvolyzing the precursor to form poly(vinyl alcohol-co-vinyl acetate) and hydrating to form the hydrogel, discs of the appropriate size are cut to form the corneal prosthesis 10.

Alternatively, the precursor of optical element 12 (prior to the solvolysis step, described in Ofstead '649, which step causes water-swelling) is formed to shape (either by molding or by lathing of a preformed button)

and solvent welded to the porous outer skirt 14 by dipping skirt 14 in a solvent (e.g., acetone) and pressing the two together. Just enough pressure is applied to make good contact between the two components 12 and 14. The precursor of element 12 is then taken through the solvolysis stage attached to skirt 14, optical element 12 retaining its shape and optical clarity.

Skirt 14 is sufficiently elastic to accommodate changes in the shape of optical element 12 during the solvolysis stage. A benefit of solvent welding is obtaining mechanical interlocking of the fibers in the hydrogel, avoiding the problem of delamination at an adhesive interface. This is especially important with a material which is going to change in size on solvolysis and swelling. Also, by avoiding the use of adhesive to bond the two together, the different materials interfacing with the human eye are limited in number. This attachment method also avoids subjecting the hydrogel to processes that might potentially change its properties.

Alternatively, optical element 12 and porous skirt 14 can be combined by using a biocompatible adhesive (e.g., cyanoacrylates) to form corneal prosthesis 10. Use of an adhesive introduces an additional material interfacing with a mammalian eye, but avoids processing techniques that can disrupt azlactone-functionality on anterior surface 17.

Coating of Prosthesis

Prior to seeding, both optical element 12 and porous skirt 14 are coated with a basement membrane component by chemical attachment reaction of the basement membrane component with the multi-functional azlactone composition covalently coupled to the anterior surface of the optical element 12. To facilitate attachment and healing when implanted, one or more of the following basement membrane components could be used: laminin, fibronectin, Type I collagen, Type IV collagen or a cell-free extract prepared from the extracellular matrix of corneal epithelial cells.

Seeding of Prosthesis

Prior to implantation of prosthesis 10 in the patient's eye, a holding device as seen in FIG. 5 of Capecchi '428 and in U.S. Pat. No. 5,032,131 (Aysta et al.), the disclosure of which is incorporated by reference, can be used to seed the basement membrane component on anterior surface 17 of optical element 12 with epithelial cells and porous skirt 14 with stromal keratocytes as described in Capecchi '428.

Implantation of Prosthesis

Prior to implantation of the prosthesis 10, it should be sterilized with ultraviolet or gamma radiation according to techniques according to those skilled in the art. Then, the prosthesis 10 is surgically implanted in the eye employing known keratectomy procedures and using fibrin adhesives generally described in Capecchi '428.

Figure 2:
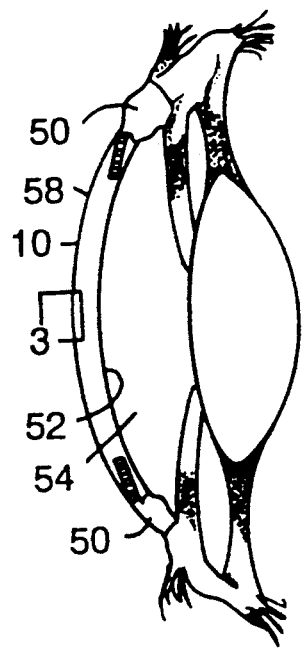
FIG. 2 is a diagrammatic sectional view of a portion of the human eye incorporating a corneal prosthesis according to the invention.
Figure 3:
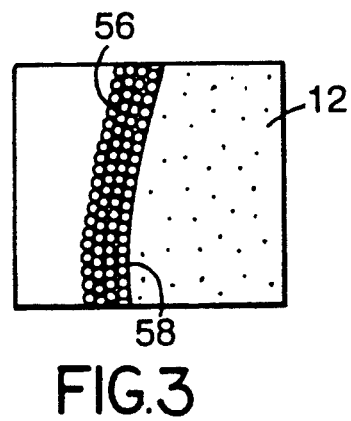
FIG. 3 is an enlarged view of a portion of FIG. 2 showing the anterior surface of the FIG. 1 prosthesis on which an epithelial layer has grown.

Referring to FIG. 2, the peripheral portion of prosthesis 10 including skirt 14 is sutured to cornea 50. Posterior surface 52 of prosthesis 10 seals anterior chamber 54, and the edge of overlying portion 18 is aligned with the epithelial layer of cornea 50, and skirt 14 is aligned with the stroma of the eye. Stromal tissue grows into the interconnected pores of porous skirt 14, serving to anchor prosthesis 10 in the patient's eye. Epithelial cells migrate from the epithelial layer of the surrounding tissue of cornea 50 to the anterior surface of optical element 12 and vice versa, forming a continuous epithelial layer 56 (see FIG. 3) on anterior surface 58 of element 12. Layer 56 desirably includes at least three cell layers and is about 50 to 100 $\mu$m thick. The preseeding of the anterior surface with epithelial cells and the preseeding of the skirt with stromal keratocytes facilitates re-epithelialization and tissue ingrowth. The complete covering of the anterior surface provides a normal precorneal tear film and a barrier against microbial invasion.

Capecchi '428 also generally describes the procedures directed to laboratory experiments employed to determine useful cell growth.

Other Embodiments

Other embodiments of the invention are within the scope of the following claims.

Nonlimiting examples of other mammalian body implants include partial thickness corneal implants, intralammelar implants, percutaneous implants, vascular grafts.

Other methods could be used to bond the porous outer skirt to the optical element. For example, the optical element could be taken through the solvolysis stage prior to bonding to the porous outer skirt.

The optical element could be formed to its desired shape when in the hydrogel state. For example, a curved optic shape for the optical element 12 can be imparted by placing the a disc of precursor polymer film of a desired thickness in a hot metal mold, preheated in an oven having a temperature of about 165° C., for about two minutes, followed by removal of the mold set and compression at about 50–100 psi during natural air cooling of the mold set. The curved optic is then solvolyzed and hydrolyzed. The optical element 12 so formed maintains curvature after hydration.

The melt blown material also has application in other implant devices and can be used to anchor members made of material that is different from the melt blown material.

The use of fibrin adhesive to inhibit epithelial downgrowth has application in other percutaneous type implants where epithelial downgrowth is a potential complication, e.g., peritoneal access devices, blood access devices, and periodontal surgery where there is a need to prevent the epithelium from migrating down the tooth-gingival interface.

Features and advantages of this invention are further illustrated by the following examples, but the particular materials and amounts thereof recited in these examples, as well as other conditions and details, should not be construed to limit this invention. Capecchi '428 Examples 1–11 describes information useful for the present invention. Specifically, the examples describe preparation of epithelial cell cultures and their seeding in vitro and in vivo, preparation of stromal keratocytes and their ingrowth in vitro and in vivo, combinations of melt blown fiber and hydrogel in vitro, use of fibrin adhesive, preparation of polyvinyltrifluoroacetate-co-maleic anhydride and conversion to hydrogels containing ionic functional groups, and preparation of melt blown fiber webs.

EXAMPLE 1

Preparation of p(VTFA/VAc) Films By Spin Casting Method; Solvolysis: Hydration: And Drying All preparations were made in a chemical fume hood. Butyl rubber or neoprene protective gloves were used while handling solvents (acetone, methanol, and ethanol) and during solvolysis steps using ammonium hydroxide/methanol solutions.

A spin casting drum powered by electric motor at 3450 rpm mounted on a 1.27 cm shaft using a 5.1×1.3 cm rubber coupling and having the following dimensions was employed: anodized aluminum lathed drum (outer dimensions: 9.5 cm diameter×14 cm length and inner dimensions: 7 cm diameter and 12.7 cm length) and lid with a polytetrafluoroethylene gasket seal and a 1 cm hole drilled in its center as an inlet for a tube to supply nitrogen into the drum.

After the drum was cleaned with a paper tissue saturated with 50% methanol/acetone solution to dissolve residue polymer remaining in drum, the drum was blotted dry with additional paper tissues. Then a clean polyester release liner (unprimed Polyester film, 2⅛"×8½", washed with acetone) was inserted into the drum. The film was seated against the drum surface by squirting 1-2 ml acetone into the spinning drum. Nitrogen flowing through the tube purged air from the drum and then the flow was adjusted to a minimum detectable amount.

Then, using a 20 ml plastic syringe, approx. 10 ml of a 30% solids of p(VTFA/VAc) in acetone solution, prepared according to Example 8 of Ofstead '649, was injected into the spinning drum. Then, a tube with a minimal, but detectable flow of nitrogen was inserted approximately halfway into the drum to maintain a low humidity, low oxygen, atmosphere. The drum was kept spinning, uninterrupted for 2-4 hours.

Then, the release film was carefully separated from the drum using a small metal spatula, and the film and the release liner were pulled from the drum carefully to avoid cracking the pVTFA/VAc film. The release liner was removed from the film. The pVTFA/VAc film was cut at the seam using scissors.

The spin casted film was protected from moisture by keeping the film in a nitrogen atmosphere, either inside a glove bag or sealed in a locking plastic bag. In some instances when longer storage times were required, pVTFA/VAc films were stored at temperature less than −20° C. To convert the p(VTFA/VAc) film to PVA film, the p(VTFA/VAc) was solvolyzed for 2 hours in 10% ammonium hydroxide/methanol solution in a beaker covered with a sealing film cover with the beaker placed in a chemical fume hood. Then the ammonium hydroxide/methanol solution was replaced with methanol and the film was soaked for an additional 2 hours in a chemical fume hood. After the methanol soaking, the film was rinsed by soaking at least four times in deionized water, with the film soaking in deionized water for minimum of 60 minutes between each rinse.

After storage of the film for at least eight hours in deionized water, the PVA film was fully hydrated. Then, the hydrated PVA film was cut into desired sample configuration with a die or scissors.

For those PVA films or discs samples which required longer storage, the films and discs samples were placed in a solution of 70% ethanol/water for 1-2 hours. Then, the 70% ethanol/water solution was replaced with absolute ethanol sufficient to cover the samples. The samples were soaked in absolute ethanol for 1-2 hours. In some instances, the samples were completely dried using six soakings in acetone for a minimum of 1 hr each. Because acetone is hygroscopic, the samples were soaked in a nitrogen-purged glove bag during the soakings. The hydrogel samples were then available in a dehydrated state, also known as a xerogel, for reaction with a multi-functional azlactone composition.

EXAMPLE 2

Preparation of Multi-Functional Azlactone Compositions

Multi-functional azlactone compositions were prepared as follows:

(a) Poly-Vinyldimethyl Azlactone (Poly-VDM) was prepared as described in "Polyazlactones" by J. K. Rasmussen, S. M. Heilmann, L. R. Krepski in *Encyclopedia of Polymer Science and Engineering*, Vol. 11, 2nd Ed., 1988, John Wiley & Sons, Inc., pp. 558-571, the disclosure of which is incorporated by reference.

(b) Oligomeric-VDM (Oligo-VDM) was prepared as described in Example 1 of U.S. Pat. No. 5,081,197, the disclosure of which is incorporated by reference.

(c) Tris[[(2-[N-2-(4,4-dimethyl-2-oxazoline-5-one-2-yl)ethyl-N-isopropyl) - 2 - amino]ethyl]amine (Tris-VDM-T) was prepared in two steps.
1. Tris(N-isopropyl - 2 - aminoethyl)amine was prepared from a mixture of tris(2-aminoethyl)amine (W. R. Grace and Co., Lexington, Mass.) (50 g), acetone (100 ml), ethanol (25 ml) and platinum oxide (Aldrich, Milwaukee, Wis.) (0.5 g) in a 500 ml pressure bottle which was hydrogenated on a Parr pressure reaction apparatus (Parr Instrument Co., Inc., Moline, Ill.) at 50 PSIG for 24 hours. The catalyst was then removed by filtration, solvent removed at reduced pressure, and the residue distilled (b.p. 113°-115° C. at 1-2 mm) to afford the desired product. The structure of the product was confirmed by NMR and IR spectoscopic analysis.
(2) (Tris-VDM-T) was prepared from a mixture of tris(N-isopropyl-2-aminoethyl)amine and 3 molar equivalents of VDM (SNPE, Princeton, N.J.) by heating at 65° C. for 18 hours to provide the desired product. Structure of the product was confirmed by spectroscopic analysis.

(d) N,N',N"-tris 2-(4,4-dimethyl-2-oxazoline-5-one-2-yl)ethyl-bis-(N,N"-isopropyl-2-aminoethyl)amine (Tris-VDM-B) was prepared in two steps,
(1) Bis(N',N"-isopropyl-2-aminoethyl)amine was prepared from bis(2-aminoethyl)amine and acetone as described in (C)(1) above.
(2) Tris-VDM-B was prepared by reaction of bis(N,-N"-isopropyl-2-aminoethyl)amine and 3 molar equivalents of VDM (SNPE, Princeton, N.J.) as described in (C)(2) above.

EXAMPLE 3

Forming An Azlactone-Functional Surface On A PVA Hydrogel Disc

Multi-functional azlactone compositions were diluted in an acetone solution to about five percent solids. Samples of PVA discs prepared and completely dried according to Example 12 were spread evenly in a glass petri dish. The discs were soaked in the multi-functional azlactone solution for 15 minutes, with gentle swirling of the solution in the petri dish to assure uniform coating of the PVA discs. Then, excess solution was decanted and the discs were spread evenly in a single layer. The petri dish was placed in a locking plastic bag containing a small amount of dessicant (Drierite ™). Then, the azlactone coated PVA disc was cured at 100° C. for 1 hour. Then, the azlactone-modified PVA discs were washed in three successive acetone soaks for about 1 hour each. The azlactone-modified PVA discs were air dried at room temperature (25° C.) in a vacuum chamber or nitrogen purged glove bag. The dried azlactone modified PVA discs were stored in a small glass sample vial, inside a foil-laminate heat sealed bag containing desiccant (Drierite ™).

EXAMPLE 4

Coupling of Protein To The Azlactone-Functional Surfaces of PVA Discs

Unhydrated azlactone modified PVA discs prepared according to Example 3 above were added to a concentrated solution of Bovine Serum Albumin ("BSA") (Fraction V commercially available from Sigma Chemical of St. Louis, Mo.) at room temperature. After 45 minutes, the discs were removed from the protein solution and washed well in a phosphate buffered saline solution. The protein-modified PVA discs were hydrated overnight at 4° C. in a phosphate buffered saline solution. Another set of unhydrated azlactone modified PVA discs prepared according to Example 3 above were reacted with Protein A (also from Sigma Chemical) according to the same techniques and conditions.

EXAMPLE 5

Preparation of Blown Microfiber Web

Polybutylene (Shell 8510, Shell Chemical Company, Houston, Tex.) and Polypropylene (Exxon 3505, Exxon Chemical Company, Houston, Tex.) were dry blended in an 80:20 ratio with a 1% by weight of Irganox 1010 antioxidant (commercially available from Ciba Geigy Corporation of Hawthorn, N.Y.) and fed to an extruder capable of melting the resins and delivering the molten resin as described in van Wente et al., "Manufacture of Superfine Organic Fibers", Naval Research Laboratory Report #4364, May 25, 1954 and in van Wente, "Superfine Thermoplastic Fibers", *Industrial Engineering Chemistry*, 48, 1342–1346, (1956) at a rate of 90–180 gr/cm die width/hr. The die had an orifice diameter of 0.033 cm (0.013 inch), an L/D ratio of 40:1 and there were 22.44 orifices per linear cm of die (57 orifices per linear inch of die). The molten polymer was extruded into a high velocity air stream created by two air knives with a 0.025 cm (0.010 inch) air gap held at 1137 Torr (22 lbs/in$^2$) and 240° C. The attenuated fibers were collected on a rotating drum held 33 cm (13 inches) from the extruder.

The resulting web had a basis weight of 45 g/m$^2$, a thickness of 0.38 mm and average fiber diameters of 5 to 8 micrometers. The resulting web was washed in a 95% ethanol solution.

Fiber diameter, basis weight and porosity can be controlled by controlling polymer feed rate, air flow rate and drum speed on the collector. Variations in the polymer blend composition or the base polymers used can also be made and processed in a similar manner.

After preparing the blown microfiber web, the web edges were cut after saturating the web in ethanol by placing the web in glass petri dish containing 95% ethanol and pressing out the air with rubber roller in order to wet the web. The web was transferred to a glass petri dish containing deionized water. Again the web was pressed with a rubber roller to assure wetting of the surface. Handling the web with long metal forceps, the web was dipped into liquid nitrogen until frozen. The frozen web was removed and immediately cut with die punch to the desired shape. The web was refrozen between cuts if multiple cuts were necessary.

EXAMPLE 6

Preparation of Corneal Prosthesis By Solvent Adhesive Method

A film of p(VTFA/VAc) having a composition of Example 1 was prepared using the spin casting method of Example 1. The sheet had a thickness of 0.05 to 0.10 mm less than the central optical element thickness ultimately desired to allow for a swell factor of 1.5–1.6×p(VTFA/VAc) thickness when the film was to be solvolyzed and hydrated. The film was removed from the spin casting drum, and the p(VTFA/VAc) film was flattened on to a polyester release liner placed on glass. Using a knife coater, a thin coating of p(VTFA/VAc) (5%–15% solids) solution dissolved in methyl ethyl ketone was spread on the spuncast p(VTFA/VAc) film. Blown microfiber web prepared according to Example 5 was cut into sheets 7.3 cm×21.6 cm (2⅞ inches33 8½ inches) and then cut again to form inner diameter holes of 4 mm diameter or rings having an 8 mm outer diameter with a 4 mm inner diameter. Then the cut blown microfiber web was positioned on the p(VTFA/VAc) film. The webs were held in position by sandwiching the composite of film and web between two glass plates while the coating of p(VTFA/VAc) dried. After sufficient time for the adhesive coating to dry completely, the glass plate was removed. Then, the composite film was solvolyzed and hydrated using the conditions of Example 1. Then discs of the desired size were cut from the film after hydration.

EXAMPLE 7

Preparation of Corneal Prosthesis by Spin Casting Method

A film of p(VTFA/VAc) of the composition of Example 1 was prepared using the spin caster drum of Example 1. The sheet had a thickness of 0.05 to 0.10 mm less than the central optical element thickness ultimately desired to allow for a swell factor of 1.5–1.6×p(VTFA/VAc) thickness when the film was to be solvolyzed and hydrated. The film remained in the spin casting drum. The blown microfiber web prepared according to Example 5 was cut to fit in the spin casting drum (7.3 cm×21.6 cm) and inner diameter holes of 4 mm diameter were punched out. The web was positioned inside the spin casting drum next to p(VTFA/VAc) film. While the drum was rotating, a small amount (2–3 ml) of acetone was injected to wet the web and to aid in flattening the web against the drum. Nitrogen flow from the tube described in Example 12 was increased to hasten evaporation of the acetone. The small amount of the acetone dissolved the surface of the p(VTFA/VAc) film, allowing the web fibers to become embedded into the film. The acetone had to be evaporated quickly to prevent the total saturation of the web and the complete dissolution of the film, which would have otherwise resulted in the web having occluded pores. Then, the spin casting drum was spun at 3450 rpm for 30–60 mins. The drum was not covered during the spinning. Then, the composite film was solvolyzed and hydrated according to the procedures of Example 1. After hydration, the corneal prosthesis discs were cut from the composite film/web to the desired size.

EXAMPLE 8

Cyanoacrylate Adhesion of Web Skirt To Azlactone-Functional Hydrogel Optical Element BSA modified PVA discs prepared according to Example 4 and blown microfiber web prepared according to Example 5 and punched to form rings according to Examples 6 and 7 were gathered for assembly into a corneal prosthesis. The BSA modified hydrated PVA disc was placed on a polyester release liner, and cyanoacrylate (CA-4 commercially available from Minnesota Mining and Manufacturing Company of St. Paul, Minn.) was brushed on to one side of the web ring. The web ring surface having cyanoacrylate adhesive was positioned onto the BSA modified PVA disc, and a second polyester release liner was placed over the prosthesis assembly with hand pressure applied for 1-2 seconds. Then, the assembly was gently peeled from the release liners and placed in distilled water to prevent curling of the prosthesis assembly. The cyanoacrylate adhesive was allowed to cure undisturbed.

EXAMPLE 9

Use of Azlactone-Functional Hydrogels To Couple Biologically Active Material Oligo-VDM (50% solids in methylethyl ketone (MEK) was coated onto p(VA/VAc) film (97.6:2.4 mole %) prepared according to Example 12 and heated for 1 hour at either 50° C., 100° C., or 150° C. In addition, a control sample was held at room temperature for the same period of time. After thorough washing with acetone, the samples were analyzed by XPS (ESCA) using an Hewlett Packard 5950B ESCA instrument, using a monochromatic x-ray source, Al K-α radiation and a beam of 800 watts. The results, shown in Table 1, indicate that the incorporation of azlactone (measured as % N) increases with increasing cure temperature. Also Table 1 shows the distribution of carbon species as measured by XPS (ESCA).

TABLE 1

ESCA ANALYSIS OF HYDROGEL DISCS COATED WITH OLIGO-VINYLDIMETHYL AZLACTONE AND HEAT TREATED FOR VARIOUS LENGTHS OF TIME

| Sample Description | Atomic Percent Composition | | | |
|---|---|---|---|---|
| | % C | % N | % O | % Si |
| Control, no heating | 67 | * | 28 | 5.6 |
| Heat 1 hr. at 50° C. | 71 | 1.3 | 26 | 1.0 |
| Heat 2 hr. at 100° C. | 71 | 1.7 | 23 | 4.4 |
| Heat 2 Hr. at 150° C. | 71 | 3.8 | 21 | 4.1 |

| Sample Description | Distribution of Carbon Species | | | | |
|---|---|---|---|---|---|
| | % C—C,C—H | % C—O | C=O | % O—C=O | N/C Ratio |
| Control, no heating | 53 | 38 | 6.1 | 2.4 | * |
| Heat 1 hr. at 50° C. | 52 | 38 | 6.8 | 3.5 | .018 |
| Heat 1 hr. at 100° C. | 61 | 30 | 5.7 | 4.0 | .014 |
| Heat 1 hr. at 150° C. | 65 | 21 | 8.5 | 5.1 | .044 |

Next, p(VA/VAc) (97.6:2.4 mole %) films (prepared according to Example 12) were coated with either poly-VDM or Oligo-VDM (30–50% in MEK), cured at 100° C. for 1 hour and washed with acetone to remove unbound resin. These samples were tested for coupling of Protein A according to procedures described in copending, coassigned U.S. patent application Ser. No. 07/609,436, the disclosure of which is incorporated by reference. The results are shown in Table 2, where RA means radioactivity.

TABLE 2

PROTEIN A COUPLING TO AZLACTONE MODIFIED P(VA/VAc) HYDROGELS

| Sample Description | Buffer Conditions | Bound RA (cpm) | Bound Protein (Total ng) | SDS Resistance (%) | Coupled Protein (Total ng) | Coupled Protein (ng/cm²) |
|---|---|---|---|---|---|---|
| Control p(VA/VAc), prequenched with ethanolamine | 0.15 M NaCl | 6.00 | 32 | 104.4 | 33 | 54.3 |
| | | 4.90 | 26 | 66.7 | 17 | 28.3 |
| | 1.5 M SO₄ | 7.85 | 41 | 62.0 | 26 | 42.2 |
| | | 4.65 | 25 | 36.6 | 9 | 14.7 |
| P(VA/VAc) coated with Oligo-VDM, prequenched with ehtanolamine | 0.15 M NaCl | 24.70 | 131 | 65.9 | 86 | 140.9 |
| | | 13.40 | 71 | 90.5 | 64 | 105.1 |
| | 0.15 M SO₄ | 22.65 | 120 | 51.4 | 61 | 100.8 |
| | | 42.9 | 227 | 59.8 | 136 | 222.3 |
| P(VA/VAc) coated with Poly-VDM prequenched with ethanolamine | 0.15 M NaCl | 10.10 | 53 | 41.6 | 22 | 36.4 |
| | | 13.55 | 72 | 50.7 | 36 | 59.5 |
| | 1.5 M SO₄ | 14.50 | 77 | 40.9 | 31 | 51.4 |
| | | 18.00 | 95 | 60.6 | 58 | 94.4 |
| Control p(VA/VAc) | 0.15 M NaCl | 11.05 | 58 | 51.0 | 30 | 48.8 |
| | | 12.55 | 66 | 38.0 | 25 | 41.3 |
| | 1.5 M SO₄ | 3.45 | 18 | 105.3 | 19 | 31.5 |
| | | 6.75 | 36 | 61.2 | 22 | 35.8 |
| P(VA/VAc) coated with Oligo-VDM | 0.15 M NaCl | 28.70 | 152 | 48.5 | 74 | 120.7 |
| | | 26.50 | 140 | 68.3 | 96 | 156.8 |
| | 1.5 M SO₄ | 15.00 | 79 | 61.1 | 48 | 79.4 |
| | | 19.50 | 103 | 53.7 | 55 | 90.7 |
| P(VA/VAc) coated with Poly-VDM | 0.15 M NaCl | 26.85 | 142 | 76.7 | 109 | 178.5 |
| | | 30.00 | 159 | 80.9 | 128 | 210.2 |
| | 1.5 M SO₄ | 37.50 | 198 | 88.7 | 176 | 288.2 |
| | | 39.95 | 190 | 86.5 | 164 | 269.4 |

As can be seen from the results, Poly-VDM and Oligo-VDM coated p(VA/VAc) films couple significantly more Protein A than the controls. Also, prequenching with ethanolamine reduces the coupling in the case of poly-VDM coated membranes; it is unclear why the ethanolamine quenched Oligo-VDM films couple high levels of Protein A.

To study the reaction of these Poly-VDM, Oligo-VDM, Tris-VDM-T, and Tris-VDM-B with PVA surfaces, a model system was used in which PVA homopolymer coated porous PE membranes (prepared according to procedures in copending, coassigned U.S. Ser. No. 07/775,969, the disclosure of which is incorporated by reference) were used as the substrate. This allowed for monitoring of the reaction by FTIR analysis of the samples in the transmission mode. The derived PVA coated membrane was dipped into a solution (approximately 5% in MEK or acetone) of the azlactone and then heated under anhydrous conditions at 100° C. At various times, the samples were removed for FTIR analysis ranging from 1 hour to 23 hours.

The reaction with Poly-VDM resulted in very minor changes in the IR spectra as measured using a Perkin-Elmer Model 1750 Infrared Fourier Transform spectrophotometer. There was an increase in absorbance at 1520 cm$^{-1}$ and 1740 cm$^{-1}$ which was due to the amide II vibration of the secondary amide and the ester linkage, respectively, in the ring opened azlactone. Three spectra after one, two and three acetone washes showed that the Poly-VDM was not eluted. In addition, there was a considerable amount of residual azlactone functionality (absorbance at 1820 cm$^{-1}$).

The reaction of Oligo-VDM with the PVA coated PE membrane at 100° C. showed a very large decrease in the azlactone absorbance (1820 cm$^{-1}$) with increases in absorbance at 1640 cm$^{-1}$ and 1520 cm$^{-1}$ (amide I and II bands) and at 1740 cm$^{-1}$ (ester carbonyl). However, upon washing with acetone, almost all of the Oligo-VDM was removed and there was no evidence of residual azlactone. The fact that very little material remains after washing was probably due to the difference in molecular weight between the polymeric- and oligomeric-VDM: the reaction of an azlactone group of Poly-VDM and a surface hydroxyl resulted in a large amount of material immobilized at the surface while with the Oligo-VDM, many more surface reactions would be required to achieve the same amount of material immobilized.

The reaction of the PVA/PE membrane with Tris-VDM-T and Tris-VDM-B found in both cases, the azlactone peak rapidly disappears and new absorbances at 1540 cm$^{-1}$, 1600 cm$^{-1}$, 1640–1660 cm$^{-1}$ and 1730 cm$^{-1}$ were indicative of the formation of ester and amide groups by reaction of the azlactone with surface hydroxyl groups. However, the azlactone absorbance was gone after about 3 hours of reaction time. The amine groups in these molecules catalyzed the reaction of the hydroxyl group with azlactone.

EXAMPLE 10

Use of Biologically Active Hydrogels To Enhance Cell Growth

Samples of p(VA/VAc) film (97.6:2.4 mole %) discs (prepared according to Example 1) were reacted with Poly-VDM and Oligo-VDM (coated with the appropriate VDM reagent, air dried and cured at 150° C. for 1 hour) and supplied to Boston University School of Medicine to study protein coupling and corneal epithelial cell attachment and growth according to procedures identified in Trinkaus-Randall et al., "Development of a Biopolymeric Keratoprosthetic Material", *Inv. Ophth. and Vis. Sci.*, 1988, Vol. 29, pp. 393–400, the disclosure of which is incorporated by reference herein. The discs were reacted with either fibronectin, laminin or type IV collagen in aqueous solution and, after washing, seeded with rabbit corneal epithelial cells which were then monitored for attachment and growth. The results showed that the cell growth on the VDM treated surfaces was improved relative to control surfaces. Specifically for fibronectin, with both Oligo-VDM and Poly-VDM cell growth numbered over 3000 per disc consistently over 10 days. For laminin, after two days, cell growth rose from about 2000 cells per disc to about 4500 cells per disc at 10 days for both Oligo-VDM and Poly-VDM. For Type IV collagen, for the first 10 days, cell growth numbered over 2000 cells per disc for Poly-VDM and rose from about 3000 cells per disc at 2 days to about 6000 cells per disc at 10 days for Oligo-VDM. By comparison, cell growth for controls of each of the three cell types declined to less than 1000 cells per disc after two days. Further, long term viability on the cell layer Was shown by a subjective determination that a stable morphology had been adopted.

COMPARATIVE EXAMPLE 11

Inability to Use Carboxylate-Functional Hydrogels to Couple Biologically Active Material Poly(vinyltrifluoroacetate-co-maleic anhydride (p(VTFA/MA)) 99.9:0.1% (w/w) was prepared as follows:

Methyltrifluoroacetate (Aldrich Chemical Co., 181.5 g), vinyltrifluoroacetate (60 g) and maleic anhydride (Aldrich Chemical Co., 0.06 g) were combined in a 500 ml roundbottom three-necked flask. The flask was fitted with a nitrogen bubbler and a dry ice/acetone condenser. Nitrogen was bubbled through the solution for 3 minutes and 3 drops Darocure 1173 initiator (E. M. Merck) were added. The reaction was stirred using a magnetic stirbar and cooled in an ice bath. Polymerization was initiated by irradiating the reaction using a sun lamp (275 Watt) held approximately 5–10 cm from the reaction flask. After 5 hours, the reaction was stopped and the product was isolated by removing the solvent and residual monomer at reduced pressure. The product was purified by dissolution in acetone and precipitation in heptane to yield p(VTFA/MA) (34.6 g) having an intrinsic viscosity of 1.32. (Polymers containing 0.05%, 0.3%, 0.5% and 1% maleic anhydride were prepared in a similar manner.) To prepare the hydrogels, each of the p(VTFA/MA) films was dissolved in acetone to make a 10% solids solution and cast into film form under a stream of dry N$_2$. The films were solvolyzed by soaking in 10% NH$_4$OH/MeOH for 2 hours followed by soaking in MeOH for 2 hours and hydration in H$_2$O. The properties of the resulting hydrogels films are listed in Table 3 below.

TABLE 3

| Wt % MA* | IV | % H$_2$O (in H$_2$O) | % H$_2$O (in saline) | Ultimate Tensile Strength kg/cm$^2$ |
| --- | --- | --- | --- | --- |
| 0.05 | 0.86 | 51.2 | 47.5 | — |
| 0.10 | 1.10 | 53.2 | 48.3 | 124.8 |
| 0.30 | 1.00 | 61.7 | 52.3 | 148.5 |
| 0.50 | 0.72 | 72.0 | 60.0 | 102.7 |
| 1.00 | 0.62 | 88.0 | 75.5 | — |

*These are the weight percents in the poly(vinyltrifluoroacetate-co-maleic anhydride copolymer). The corresponding mole percents are 0.07%, 0.14, 0.43, 0.70 and 1.4.

Cell growth on these samples increased from about 3000 cells after three days to a range of 6000 to 12,000 after five days for polymer compositions with three different MA mole percents: 0.07; 0.14; and 0.43. But cells died after five days to less than 3000 cells after seven days and less than about 2000 cells after 10 days.

Further, subjective evaluation determined that the cells on the p(VA/MA) surface tended to "round up" and were not as adherent to the polymer surface as a surface employing azlactone functionality to couple biologically active material for enhancing cell growth.

EXAMPLE 12

Use of Azlactone-Functional Materials On A Cellulose Substrate

Squares of cellulose filter paper (Whatman #4 commercially available from Whatman Ltd. of Maidstone, England) were dried at 100° C. over Drierite ™ desiccant and treated by soaking for 5 minutes in one of the following solutions (four samples per set):
A) 5% polyVDM in methylethyl ketone (MEK)
B) 5% Oligo-VDM in MEK
C) Tris-VDM-T in MEK
D) Tris-VDM-B in MEK The samples were allowed to air dry (under dry $N_2$) for 10 minutes and one sample was taken from each set and washed extensively with MEK (and labeled samples A1 to D1).

The remaining samples were heated under dry conditions at 100° C. and samples were removed after 30 minutes (labeled as samples A2 to D2), 60 minutes (labeled as samples A3 to D3) and 90 minutes (labeled as samples A4 to D4). All samples were extensively washed with MEK and dried under dry $N_2$.

XPS (ESCA) analysis is reported in TABLE 4.

TABLE 4

| Sample ID | Treatment Conditions | % C | % N | % O | Other Elements Detected |
|---|---|---|---|---|---|
| A1 | No heat | 59.78 | 3.17 | 37.05 | None |
| A2 | 30 min @ 100° C. | 61.21 | 6.40 | 32.39 | None |
| A3 | 60 min @ 100° C. | 61.88 | 5.08 | 33.04 | None |
| A4 | 90 min @ 100° C. | 62.91 | 4.44 | 32.65 | None |
| B1 | No heat | 54.19 | 1.58 | 44.23 | None |
| B2 | 30 min @ 100° C. | 56.86 | 2.80 | 40.34 | None |
| B3 | 60 min @ 100° C. | 56.19 | 2.02 | 41.79 | None |
| B4 | 90 min @ 100° C. | 55.92 | 2.32 | 41.76 | None |
| C1 | No heat | 57.05 | 1.66 | 41.29 | None |
| C2 | 30 min @ 100° C. | 67.50 | 3.90 | 28.60 | None |
| C3 | 60 min @ 100° C. | 656.73 | 2.96 | 40.30 | None |
| C4 | 90 min @ 100° C. | 661.64 | 5.12 | 33.23 | None |
| D1 | No heat | 56.55 | 3.82 | 39.63 | None |
| D2 | 30 min @ 100° C. | 57.84 | 3.28 | 38.88 | None |
| D3 | 60 min @ 100° C. | 56.64 | 3.85 | 38.28 | 1.22% Mg |
| D4 | 90 min @ 100° C. | 61.34 | 6.85 | 31.81 | None |
| Control (unmodified Whatman #4 filter paper) | | 55.26 | 0.00 | 44.72 | None |

The samples were then analyzed by Diffuse Reflectance Infra-red Fourier Transfer (DRIFT) spectroscopy (using a Perkin Elmer Model 1750 spectrophotometer) using as the background spectra a sample of unmodified Whatman #4 paper (i.e., this results in a difference spectra between the test sample and the unmodified paper). The Poly-VDM treated samples showed a weak 1820 cm$^{-1}$ peak for all heated samples. (The 1820 cm$^{-1}$ peak is characteristic of the azlactone moiety.) The Oligo-VDM treated (samples B1 to B4) and the Tris-VDM-T (samples C1 to C4) samples showed trace absorption of 1820 cm$^{-1}$. In samples D1 to D4 the azlactone absorption could not be detected by this method.

To demonstrate covalent coupling to the immobilized azlactone, Whatman #4 filter paper was coated with Poly-VDM by soaking in a 33% solids solution for 15 minutes, draining excess solution, heating for 1 hour at 100° C., washing extensively with MEK, and air drying under dry $N_2$. Samples were then reacted in aqueous solution at pH 9.0, 1.5M in $K_2SO_4$ containing either 0.1M Cl(CH$_2$)$_3$NH$_2$ HCl or CH$_3$CH$_2$SCH$_2$CH$_2$NH$_2$ HCl (reacted at room temperature for 2 hours). As a control, samples were also pre-quenched by reaction in 0.1M Ethanolamine pH 9.0, 1.5M $K_2SO_4$ for 2 hours at room temperature, washed with $H_2O$ and reacted with the chloropropylamine solution and the ethylthioethylamine solution described above for 4 hours at room temperature. All samples were then analyzed by XPS (ESCA) and the results are shown below in TABLE 5:

TABLE 5

| Sample ID | Treatment Conditions | % C | % N | % O | Other Elements Detected |
|---|---|---|---|---|---|
| Whatman #4 paper (control) | | 54.42 | 0.00 | 45.58 | None |
| Poly-VDM treated Whatman #4 | | 66.78 | 8.96 | 24.27 | None |
| Poly-VDM/Whatman #4 reacted with Chloropropylamine | | 62.76 | 10.25 | 21.84 | 5.15% Cl |
| Ply-VDM/Whatman #4, prequenched by reaction with ethanolamine followed by reaction with Chloropropylamine | | 62.81 | 10.08 | 27.11 | None |
| Poly-VDM/Whatman #4 reacted with Ethylthioethylamine | | 65.57 | 9.26 | 21.59 | 3.48% S |
| Poly-VDM/Whatman #4, prequenched by reaction with ethanolamine followed by reaction with Chloropropylamine | | 63.58 | 11.58 | 24.84 | None |

EXAMPLE 13

Preparation of Ultraviolet Light Absorbing Compositions 2-allyloxy-4,4'-dimethoxy-2-hydroxy benzophenone (2-allyloxy-BP), and 3-allyl-2,2'-dihydroxy-4,4'-dimethoxy benzophenone (3-allyl-BP) are prepared according to the following process. To 89 grams of 2,2'-dihydroxy-4,4'-dimethoxy benzophenone is added 39 grams allylbromide, 165 grams of potassium carbonate and 400 ml of acetone. The mixture was refluxed for three hours, cooled to room temperature and the resulting salt was filtered out from the solution. The filtrate was concentrated to a residual oil, water and methylene chloride were added, and the organic layer was extracted. The extract was washed several additional times with water. The methylene chloride was dried with magnesium sulfate and the solvent was evaporated under vacuum to produce about 94 grams of brown-colored oil comprising 2-allyloxy-BP.

The 3-allyl-BP was synthesized by placing 10 grams of the brown-colored oil in a round bottom flask. The flask was placed in an oil bath at 240° C. After 30 minutes of heating with stirring, the material is cooled to room temperature and 20 ml of methanol was added. As the solution cooled, a yellow solid precipitated. Recrystallization twice from methanol produced 2.5 grams of 3-allyl-BP having a melting point of about 70°-71° C.

EXAMPLE 14

Preparation of Ultraviolet Light Absorbing Hydrogel Compositions by Blending

The following compounds were gathered and placed in a reaction vessel: 10 grams of VTFA prepared according to Example 1 of PCT Publication WO 92/07899 (Gagnon et al.) the disclosure of which is incorporated by reference, 0.025 grams of 3-allyl-BP prepared according to Example 13 above, 0.02 grams of Di (sec-butyl) peroxydicarbonate initiator commercially available as Lupersol 225 from Pennwalt, and 10 grams of Freon TF. The reaction vessel was heated at 40° C. for 12 hours and then at 60° C. for 3 hours to yield poly(VTFA/3-allyl-BP). The yield was 84%. Other experiments showed the yield decreased to 6% as the amount of 3-allyl-BP in the formulation increased to 1.0 weight percent. Poly(VTFA/3-allyl-BP) was then dissolved in acetone (30 weight percent) and then was blended with 30 weight percent solids of p(VFTA/VAc) in acetone solution prepared according to Example 8 of Ofstead '649 in blend ratios ranging from 50:50 to 90:10 (p(VTFA/VAc):p(VTFA/3-allyl-BP)). The solution was well mixed and cast on a glass plate. A thin, very tough, film, approximately 0.4 mm thick, was obtained. After solvolysis and hydration, water uptake in percent ranged from 59.2% for the 50:50 blend to 63.1% for the 90:10 blend. By comparison, an unblended p(VA/VAc) film had a water uptake of 68.2%.

EXAMPLE 15

Preparation of Ultraviolet Light Absorbing Hydrogel Compositions by Copolymerization The following compounds were gathered and placed in a reaction vessel: 9.85 grams of VTFA prepared according to Example 1 of PCT Publication WO 92/07899, 0.025 grams of 3-allyl-BP prepared according to Example 13 above, 0.02 grams of Di (sec-butyl) peroxydicarbonate initiator commercially available as Lupersol 225 from Pennwalt, and 0.015 grams of maleic anhydride (MA). The reaction vessel was heated at 40° C. for 12 hours and then at 60° C. for 3 hours to yield poly(VTFA/3-allyl-BP/MA). The yield was 98.3%. In a second experiment, the reaction vessel charged with twice the amount of 3-allyl-BP reduced the yield to 48.4%. The resulting copolymer was dissolved in acetone (30% by weight of solids) and prepared into a film in the same manner as described for blended compositions of Example 14 above. After solvolysis and hydration, the water uptake was 57.2% for the copolymer prepared from 0.25 weight percent of 3-allyl-BP and 78.5% for the copolymer prepared from 0.50 weight percent of 3-allyl-BP.

For an appreciation of the scope of the invention, the claims follow.

What is claimed is:

1. A mammalian body implant comprising: a hydrogel having azlactone-reactive nucleophilic surfaces, a multi-functional azlactone composition covalently coupled using at least one azlactone moiety to the azlactone-reactive nucleophilic surfaces, and a biologically active material coupled to the multi-functional azlactone composition using at least one azlactone moiety; wherein the mammalian body implant has the formula:

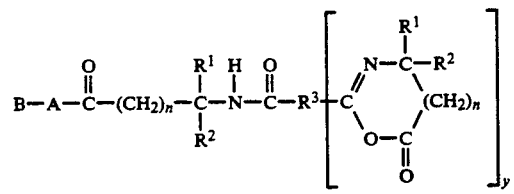

wherein $R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon atoms and 0 to 3 S, N, and nonperoxidic O heteroatoms, or $R^1$ and $R^2$ taken together with the carbon to which they are joined can form a carbocyclic ring containing 4 to 12 ring atoms, and n is an integer 0 or 1;

wherein y is at least one and is the number of azlactone moieties less at least one;

wherein $R^3$ is a bridging group capable of covalently connecting a plurality of azlactone moieties; and wherein B is the hydrogel having azlactone-reactive nucleophilic surfaces and A is a residue of a azlactone-reactive nucleophilic group on the surface on the hydrogel, the azlactone-reactive nucleophilic group comprising O, S, or $NR^4$, and wherein $R^4$ is hydrogen or an alkyl group containing from 1 to 4 carbon atoms.

2. The mammalian body implant according to claim 1, wherein the implant comprises a corneal prosthesis.

3. The mammalian body implant according to claim 1, wherein the implant comprises a corneal prosthesis and wherein the biologically active material comprises laminin, fibronectin, Type I collagen, Type IV collagen, a cell-free extract prepared from an extracellular matrix of corneal epithelial cells, or combinations thereof.

4. The mammalian body implant according to claim 1, wherein the implant comprises a corneal prosthesis and wherein the hydrogel comprises a poly(vinyl alcohol) copolymer.

5. The mammalian body implant according to claim 1, wherein the implant comprises a corneal prosthesis and further comprising a layer of epithethial cells adhered to the nucleophilic surfaces at the biologically active material.

6. The mammalian body implant according to claim 2, wherein the corneal prosthesis comprises a blend of a poly(vinyl alcohol-co-vinyl acetate) and a copolymer of poly(vinyl alcohol) and a benzophenone ultraviolet light absorber selected from the group consisting of 2-allyloxy-4,4'-dimethoxy-2-hydroxy benzophenone, 3-allyl-2,2'-dihydroxy-4,4'-dimethoxy benzophenone, 2,2'-dihydroxy-4-methoxy-4'-(2-methacryloyloxyethoxy) benzophenone and 4-(2'-acryloyloxyethoxy)-2-hydroxy benzophenone.

7. The mammalian body implant according to claim 2, wherein the corneal prosthesis comprises an optical element which comprises a copolymer of poly(vinyl alcohol), a benzophenone ultraviolet light absorber selected from the group consisting of 2-allyloxy-4,4'-dimethoxy-2'-hydroxy benzophenone and 3-allyl-2,2'-dihydroxy-4,4'-dimethoxy benzophenone, and a comonomer comprising maleic anhydride.

8. The mammalian body implant according to claim 2, wherein the corneal prosthesis comprises an optical element having an optically transparent central portion and an anterior surface having the reaction product of the multi-azlactone composition and the biologically active material, wherein the anterior surface is capable of supporting a layer of epithethial cells, and a porous outer skirt secured to the periphery of the optical element, the skirt being sufficiently porous to permit cell ingrowth and tissue attachment.

9. The mammalian body implant according to claim 8, wherein the biologically active material comprises laminin, fibronectin, Type I collagen, Type IV collagen, a cell-free extract prepared from an extracellular matrix of corneal epithelial cells, or combinations thereof.

10. The mammalian body implant according to claim 8, wherein the hydrogel comprises a poly(vinyl alcohol) copolymer.

11. The mammalian body implant according to claim 8, further comprising a layer of epithethial cells adhered to the nucleophilic surfaces at the biologically active material.

12. The mammalian body implant according to claim 8, wherein the porous outer skirt comprises a coherent mass of randomly-oriented melt drawn fibers having an interconnected network of pores.

13. The mammalian body implant according to claim 8, wherein the optical element is a poly(vinyl alcohol-co-vinyl acetate) copolymer and the porous outer skirt is a polyolefin material, and
   wherein the multi-functional azlactone composition, prior to covalent coupling to the azlactone-reactive nucleophilic surfaces, comprises 2-alkenyl azlactone homopolymers, copolymers, or oligomers, tris [[2-[N-2-(4,4-dimethyl-2-oxazoline-5-one-2-yl)ethyl, N-isopropyl]-2-amino]ethyl]amine, or N,N', N''-tris-2-(4,4-dimethyl-2-oxazoline-5-one-2-yl)ethyl-bis-(N,N''-isopropyl-2-aminoethyl)amine.

14. The mammalian body implant according to claim 13, wherein the optical element has an anterior surface coated with epithethial cells.

15. An azlactone-functional substrate, comprising a substrate having azlactone-reactive nucleophilic surfaces, said substrate selected from the group consisting of cellulose; modified cellulose derivatives; agarose; dextran; chitin; chitosan; polymers derived from hydroxyethyl methacrylate, hydroxypropyl acrylate, N-methylol acrylamide, allyl alcohol, allyl amine, or N-[3-(N'-isopropyl) aminopropyl] methacrylamide monomers; poly(vinyl alcohol) homopolymers; and poly(vinyl alcohol) copolymers, and a multi-functional azlactone composition covalently coupled thereto using at least one azlactone moiety in a manner such that at least one azlactone moiety remains available for further nucleophilic reaction;
   wherein the azlactone-functional substrate has the formula:

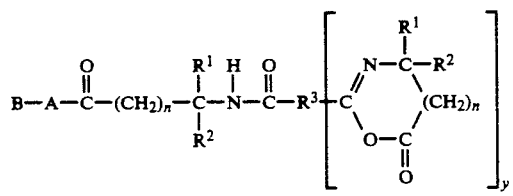

wherein $R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon atoms and 0 to 3 S, N, and nonperoxidic O heteroatoms, or $R^1$ and $R^2$ taken together with the carbon to which they are joined can form a carbocyclic ring containing 4 to 12 ring atoms, and n is an integer 0 or 1;
   wherein y is at least one and is the number of azlactone moieties less at least one;
   wherein $R^3$ is a bridging group capable of covalently connecting a plurality of azlactone moieties; and
   wherein B is the substrate having azlactone-reactive nucleophilic surfaces and A is a residue of a azlactone-reactive nucleophilic group on the surface on the substrate, the azlactone-reactive nucleophilic group comprising O, S, or $NR^4$, and wherein $R^4$ is hydrogen or an alkyl group containing from 1 to 4 carbon atoms.

16. The azlactone-functional substrate, according to claim 15 wherein the multi-functional azlactone composition comprises 2-alkenyl azlactone homopolymers, copolymers, or oligomers, tris[[2-[N-2(4,4-dimethyl-2-oxazoline-5-one-2-yl)ethyl, N-isopropyl]-2-amino]ethyl]amine, or N,N', N''-tris-2-(4,4-dimethyl-2-oxazoline-5-one-2-yl)ethyl-bis-(N,N''-isopropyl-2-aminoethyl)amine.

17. The azlactone-functional substrate, according to claim 15 wherein the substrate comprises a natural or synthetic composition which has azlactone-reactive, nucleophilic surfaces due to the presence of azlactone-reactive, nucleophilic moieties comprising hydroxyl, amine, or thiol moieties.

18. The azlactone-functional substrate, according to claim 17, wherein the substrate comprises cellulose, modified cellulose derivatives, agarose, dextran, chitin, chitosan, polymers derived from monomers comprising hydroxyethyl methacrylate, hydroxypropyl acrylate, N-methylolacrylamide, allyl alcohol, allyl amine, and N-[3-(N'-isopropyl)aminopropyl] methacrylamide, and polymers derived by modification of polymers such as silica gel and glass particles reacted with γ-triethoxysilylpropylamine, γ-triethoxysilylpropane-1-thiol, or γ-glycidoxypropyltrimethoxysilane after hydroylsis of epoxide moieties thereon.

19. The azlactone-functional substrate, according to claim 15, wherein the substrate is a hydrogel which comprises a poly(vinyl alcohol) copolymer.

20. The azlactone-functional substrate, according to claim 19, wherein the poly(vinyl alcohol) copolymer comprises vinyl alcohol and vinyl acetate in molar ratio of from about 99.9:0.1 vinyl alcohol:vinyl acetate to about 95:5.

21. The azlactone-functional substrate, according to claim 19, wherein the poly(vinyl alcohol) copolymer comprises vinyl alcohol and vinyl acetate in molar ratio of from about 97:3 vinyl alcohol:vinyl acetate to about 99:1.

22. A biologically active substrate, comprising the reaction product of an azlactone-functional substrate and a biologically active material, wherein the azlactone-functional substrate comprises a substrate having azlactone-reactive nucleophilic surfaces and a multi-functional azlactone composition covalently coupled thereto using at least one azlactone moiety, and wherein the biologically active material is coupled using at least one azlactone moiety to the multifunctional azlactone composition, wherein the azlactone-functional substrate has the same formula as that of claim 19.

23. An activated substrate having the formula:

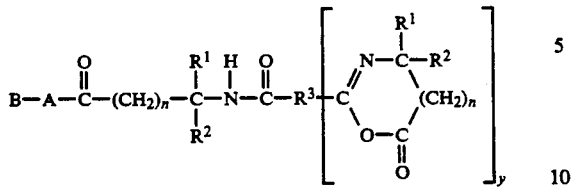

wherein $R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon atoms and 0 to 3 S, N, and nonperoxidic O heteroatoms, or $R^1$ and $R^2$ taken together with the carbon to which they are joined can form a carbocyclic ring containing 4 to 12 ring atoms, and n is an integer 0 or 1;

wherein y is at least one and is the number of azlactone moieties less at least one;

wherein $R^3$ is a bridging group capable of covalently connecting a plurality of azlactone moieties; and wherein B is a substrate having azlactone-reactive nucleophilic surfaces and A is a residue of a azlactone-reactive nucleophilic group on the surface on the substrate, the azlactone-functional nucleophilic group comprising O, S; or $NR^4$, wherein $R^4$ is hydrogen or an alkyl group containing from 1 to 4 carbon atoms, and wherein the substrate is selected from the group consisting of cellulose; modified cellulose derivatives; agarose; dextran; chitin; chitosan; polymers derived from hydroxyethyl methacrylate, hydroxypropyl acrylate, N-methylol acrylamide, allyl alcohol, allyl amine, or N-[3-(N'-isopropyl) aminopropyl] methacrylamide monomers; poly(vinyl alcohol) homopolymers; and poly(vinyl alcohol) copolymers.

24. The activated substrate according to claim 23, wherein $R^3$ comprises an alkylene group having up to 14 carbon atoms; an arylene group having up to 10 carbon atoms; a cycloalkylene group having up to 6 carbon atoms; groups resulting from a Michael reaction of a Michael donor nucleophilic compound with a plurality of 2-alkenyl azlactone Michael acceptors, wherein the Michael donor nucleophilic compound has at least two azlactone-reactive moieties; or combinations thereof.

25. The activated substrate according to claim 24, wherein the Michael donor nucleophilic compounds comprise thiols, secondary amines, carbon acids, enamines, imides, nitrogen heterocycles, or combinations thereof.

26. A method of making an azlactone-functional hydrogel, comprising the steps of:
(a) forming a hydrogel in a dehydrated state comprising a composition having azlactone-reactive nucleophilic surfaces;
(b) reacting a multi-functional azlactone composition with the azlactone-reactive nucleophilic surfaces of the hydrogel in a dehydrated state in a manner that retains at least one azlactone moiety remaining available for further nucleophilic reaction;

wherein the azlactone-functional hydrogel has the formula:

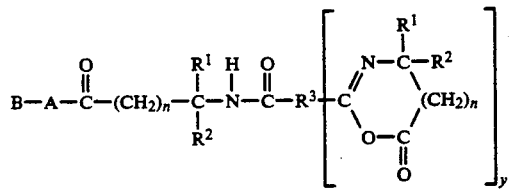

wherein $R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon atoms and 0 to 3 S, N, and nonperoxidic O heteroatoms, or $R^1$ and $R^2$ taken together with the carbon to which they are joined can form a carbocyclic ring containing 4 to 12 ring atoms, and n is an integer 0 or 1;

wherein y is at least one and is the number of azlactone moieties less at least one;

wherein $R^3$ is a bridging group capable of covalently connecting a plurality of azlactone moieties; and wherein B is the hydrogel having azlactone-reactive nucleophilic surfaces and A is a residue of a azlactone-reactive nucleophilic group on the surface on the hydrogel, the azlactone-reactive nucleophilic group comprising, O, S, or $NR^4$, and wherein $R^4$ is hydrogen or an alkyl group containing from 1 to 4 carbon atoms.

27. A method of forming a mammalian body implant, comprising the steps of:
(a) forming an azlactone-functional hydrogel according to the method of claim 26 and
(b) reacting a biologically active material with at least one azlactone moiety.

28. The method according to claim 27, further comprising after the reacting step, the step of covering the biologically active material with mammalian cells.

29. The method according to claim 27, wherein the implant comprises a corneal prosthesis and wherein the hydrogel comprises an optical element having a periphery, and wherein the method further comprises the step of securing a porous outer skirt to the periphery.

30. The mammalian body implant according to claim 1, wherein the bridging group comprises an alkylene group having up to 14 carbon atoms; an arylene group having up to 10 carbon atoms; a cycloalkylene group having up to 6 carbon atoms; a group resulting from a Michael reaction of a Michael donor nucleophilic compound with a plurality of 2-alkenyl azlactone Michael acceptors, where the Michael donor nucleophilic compound has at least two azlactone-reactive moieties; or combinations thereof.

31. The mammalian body implant according to claim 8, wherein the bridging group comprises an alkylene group having up to 14 carbon atoms; an arylene group having up to 10 carbon atoms; a cycloalkylene group having up to 6 carbon atoms; a group resulting from a Michael reaction of a Michael donor nucleophilic compound with a plurality of 2-alkenyl azlactone Michael acceptors, where the Michael donor nucleophilic compound has at least two azlactone-reactive moieties; or combinations thereof.

32. The mammalian body implant according to claim 15, wherein the bridging group comprises an alkylene group having up to 14 carbon atoms; an arylene group having up to 10 carbon atoms; a cycloalkylene group having up to 6 carbon atoms; a group resulting from a Michael reaction of a Michael donor nucleophilic compound with a plurality of 2-alkenyl azlactone Michael acceptors, where the Michael donor nucleophilic compound has at least two azlactone-reactive moieties; or combinations thereof.

* * * * *